United States Patent [19]

Feldman et al.

[11] Patent Number: 4,876,241
[45] Date of Patent: Oct. 24, 1989

[54] STABILIZATION OF BIOLOGICAL AND PHARMACEUTICAL PRODUCTS DURING THERMAL INACTIVATION OF VIRAL AND BACTERIAL CONTAMINANTS

[75] Inventors: Fred Feldman, Park Forest; Mark S. Klekamp, Bourbonnais, both of Ill.; Michael E. Hrinda, Gwynedd Valley; Arthur B. Shaw, Audubon, both of Pa.; Sudhish Chandra, Kankakee, Ill.

[73] Assignee: Armour Pharmaceutical Company, Fort Washington, Pa.

[21] Appl. No.: 195,318

[22] Filed: May 18, 1988

Related U.S. Application Data

[63] Continuation-in-part of Ser. No. 52,926, May 22, 1987.

[51] Int. Cl.$^4$ ............................................. A61K 37/02
[52] U.S. Cl. ........................................ 514/2; 424/101; 514/3; 514/6; 514/7; 514/8
[58] Field of Search ................... 424/101; 514/2, 3, 6, 514/7, 8

[56] References Cited

U.S. PATENT DOCUMENTS

| | | |
|---|---|---|
| 4,297,344 | 10/1981 | Schwinn . |
| 4,314,997 | 2/1982 | Shanbrom . |
| 4,379,085 | 4/1983 | Williams et al. . |
| 4,405,603 | 9/1983 | Schwinn et al. . |
| 4,440,679 | 4/1984 | Fernandes et al. . |
| 4,446,134 | 5/1984 | Naito et al. ......................... 424/101 |
| 4,456,590 | 6/1984 | Rubinstein . |
| 4,470,968 | 9/1984 | Mitra et al. . |
| 4,585,654 | 4/1986 | Landaburu et al. . |
| 4,673,733 | 6/1987 | Chandra et al. . |
| 4,721,777 | 1/1988 | Wemura et al. .................... 424/101 |

OTHER PUBLICATIONS

White, G. C., Matthews, T. J., Weinhold, K. J., Haynes, B. F., Cromartie, H. L., McMillan, C. W., and Bolognesi, D. P. (1986), Lancet I, pp. 611-612.
Van Den Berg, W., Ten Cate, J. W., Breederveld, C., and Goudsmit, J. (1986), Lancet I, pp. 803-804.
Colombo, M., Carnelli, V., Gazengel, C., Mannucci, P. M., Savidge, G. F., and Schimpf, K. (1985), Lancet II, pp 1-4.
Preston, F. E., Hay, C. R. M., Dewar, M. S., Greaves, M., Triger, D. R. (1985), Lancet II, p. 213.
McDougal, J. S., Martin, L. S., Cort, S. P., Mozen, M., Heldebrant, C. M., and Evatt, B. L. (1985), J. Clinical Investigation, 76, pp. 875-877.
Hilfenhaus, J., Mauler, R., Friis, R., and Bauer, H. (1985), Proceedings of the Society for Experimental Biology and Medicine, 178, pp. 580-584.
Hilfenhaus, J., Herrmann, A., Mauler, R., and Prince, A. M. (1986), Vox Sang., 50, pp. 208-211.
Hilfenhaus, J., and Weidmann, E. (1986), Drug Research, 36, pp. 621-625.
Piszkiewicz, D., Apfelzweig, R., Bourett, L., Hattley, K., Cabradilla, C. D., McDougal, J. S., and Menache, D. (1988), Transfusion, 28, pp. 198-199.
Mosseler, J., Schimpf, K., Auerswald, G., Bayer, H., Schneider, J., and Hunsmann, G. (1985), Lancet I, p. 1111.

Primary Examiner—Sam Rosen

[57] ABSTRACT

A method of inactivating pathogens in proteinaceous biological and pharmaceutical products which comprises: mixing the product in an aqueous solution with one or more primary stabilizers selected from the group consisting of sugars and sugar alcohols and one or more secondary stabilizers selected from the group consisting of sodium acetate, potassium acetate, lithium acetate, magnesium acetate, ammonium acetate, barium acetate, sodium sulfate, ammonium sulfate, lithium sulfate, potassium sulfate and magnesium sulfate; and subjecting said aqueous solution to a pathogen inactivating process.

32 Claims, No Drawings

STABILIZATION OF BIOLOGICAL AND PHARMACEUTICAL PRODUCTS DURING THERMAL INACTIVATION OF VIRAL AND BACTERIAL CONTAMINANTS

This is a continuation-in-part application of copending application Ser. No. 052,926, filed May 22, 1987.

BACKGROUND OF THE INVENTION

1. Field of the Invention

This invention relates to a process of stabilizing biological and pharmaceutical products in order to protect their activity during treatment designed to inactivate viral and/or bacterial contaminants. More particularly, the invention relates to the stabilization of proteinaceous materials that are to be rendered free of biological contaminants such as viruses and the like, and especially Epstein-Barr Virus (EBV) and cytomegalovirus (CMV), infectious hepatitis viruses, such as hepatitis B virus (HBV), non-A non-B hepatitis virus (NANBV), and the Human Immunodeficiency Virus (HTLV III/LAV/HIV) which causes AIDS Biological and pharmaceutical products may be contaminated, or are suspect of being contaminated by viruses and bacteria which render them unsuitable and often quite dangerous for therapeutic use. Such contamination can be a source of contagious diseases posing great risk to the users of such products.

It is possible to inactivate the viral and bacterial contaminants in the initial or intermediate stages of production or in the final products. The inactivation procedures, however, are very harsh and usually result in a substantial loss of activity of labile biologicals and pharmaceuticals. Therefore, prior to inactivation of the contaminants, it is necessary to stabilize the biologicals and pharmaceuticals to protect their activity.

In its general aspect, this invention relates to the stabilization of biological and pharmaceutical products in the liquid or suspension state while rendering them free of viral and bacterial contaminants using thermal, chemical or irradiation methods of inactivation.

In a specific aspect, the invention relates to the production of biological and pharmaceutical products to be pasteurized in the liquid state during the manufacturing or purification process.

Liquid pasteurization is an established method for inactivating pathogenic microorganisms which contaminate products derived from biological materials, such as human plasma. Specifically, this invention relates to the use of stabilizers which prevent inactivation of proteins and allow pasteurization to be performed with minimal loss of biological and therapeutic activity. Stabilization is achieved by the addition of appropriate amounts of one or more mono-, di-, or tri-saccharides or sugar alchohols in combination with one or more neutral salts prior to pasteurization.

Description of the Prior Art

Agents derived from biological sources designed for therapeutic, prophylactic or diagnostic use constitute a large and important segment of products used in health care. Examples of such products and uses thereof include the following: Factor VIII is used to treat hemophelia; immune serum globulin is employed in the treatment of congenital gamma globulin deficiency, poliomyletitis and hepatitis A and B; antithrombin III is a coagulation inhibitor; plasminogen-streptokinase complex is used in the treatment of thromboembolism; and plasma growth hormone corrects pituitary growth deficiency.

An important concern associated with the use of therapeutic agents derived from biological sources is the transmission of disease, especially viral disease. Prevalent viral contaminants include hepatitis B virus (HBV), non-A, non-B hepatitis virus (NANBV), and HTLV III/LAV/HIV, which cause AIDS. In order to ensure that products produced from biological sources are virus-safe, various methodologies have been proposed for virus inactivation. These, in general, can be summarized as methods of: heating of the blood products in aqueous solution, if desired, with the addition of virucidal substances; heating of the blood products in aqueous solution in the presence of stabilizing agents; treating the blood products with organic solvents; irradiating the blood products in the solid state; and heating of the blood products in the dry state.

All these methods aim at destroying the potential viral and bacterial infectivity of the preparations while substantially maintaining their desired biological activity.

Representative methods of the prior art believed to be relevant to the present invention are as follows:

U.S. Pat. No. 4,456,590 (Rubenstein) relates to a method of heat treatment of plasma fractions in lyophilized form for the purpose of inactivating hepatitis virus that may be present in the fractions.

U.S. Pat. No. 4,314,997 (Shanbrom) teaches a chemical inactivation process by which plasma and plasma derivatives in solution or suspension are contacted with a non-denaturing amphiphile, i.e., a surface active agent, to cause irreversible destruction of endotoxins and inactivation of hepatitis viruses.

U.S. Pat. No. 4,440,679 (Fernandes et al.) describes a method wherein therapeutically active proteins are pasteurized by mixing the protein composition with a pasteurization stabilizing amount of a polyol prior to pasteurization.

U.S. Pat. No. 4,297,344 (Schwinn et al.) discloses a process for the stabilization against heat of the coagulation Factors II, VIII, XIII, antithrombin III and plasminogen, in aqueous solution, which comprises adding to the solution both an aminoacid and one or more of a monosaccharide, an oligosaccharide or a sugar alcohol.

U.S. Pat. No. 4,585,654 (Landaburu et al.) pertains to a process of inactivating viruses in plasma protein solutions by heating the same in the presence of a polyol, a surface active agent and a chelating agent.

It appears, according to some investigators, that wet heating of certain biological products is more effective than dry heating. For example, in a comparison of wet heating against dry heat treatment for safety from NANBV transmission, results suggested that wet heating provided a higher degree of safety (Kernoff et al., The Lancet, Sept. 28, 1985, p. 721). Clinical data shows that Factor VIII concentrate pasteurized in a liquid phase transmitted no HBV, NANBV, or HTLV III/-LAV/HIV in more than six years of clinical experience. (International Congress of the World Federation of Hemophelia, June 8-13 (1986); N. Heimburger: "Preparation of a F VIII concentrate free from pathogenic viruses.") The efficacy of liquid pasteurization in virus inactivation is perhaps best demonstrated by the history of serum albumin, where no case of serum hepatitis has been traced to transfusion of heated albumin over a period of more than thirty five years. ("Milestones in Blood Transfusion and Immunohaemotology", Vox Sang 46:338-340 (1984)).

Direct demonstration of viral inactivation by pasteurization in the liquid state has shown that cytomegalovirus, Epstein-Barr virus, herpes simplex virus, poliovirus, vaccinia virus, hepatitis B virus, non-A non-B hepatitis virus, and HTLV III/LAV/HIV are all inactivated, and further, that neoantigens are not formed during liquid-state pasteurization ("Pasteurization as an Efficient Method to Inactivate Blood Borne Viruses in Factor VIII Concentrates", J. Hilfenhous and E. Weidman; Arzneim.-Forsch/Drug Res. 36(I) Nr. 4 (1986)).

Given that liquid pasteurization is a proven means of inactivating viral contaminants, it becomes necessary to stabilize thermally sensitive bioactive molecules from heat inactivation. The object of this invention is the liquid pasteurization of biological and pharmaceutical products. Stabilization against the thermal inactivation of these products is achieved through the use of one or more mono-, di-, or tri-saccharides, or sugar alcohols in combination with one or more neutral salts.

This method significantly differs from the closest resembling methods of the prior art references described above. To wit:

(a) It differs from the method of using the combination of monosaccharides, oligosaccharides or sugar alcohols with amino acids or certain amino acid analogs by the replacement of amino acids and their analogs with a neutral salt. There are distinct advantages associated with this replacement. First, the addition of stabilizing amounts of amino acids to a biological or pharmaceutical product may cause inactivation due to abrupt and often significant pH changes. This effect is minimized or eliminated through the use of stabilizing salts. Second, many amino acids are sparingly soluble in aqueous solvents whereas most stabilizing salts are quite soluble, allowing the addition of higher concentrations of stabilizers. Third, when using amino acids as stabilizers it is necessary to remove all residual stabilizer from the final product as intensive therapy with a pharmaceutical product containing residual amino acid could overload the body's detoxification system in patients with severe liver or kidney damage.

(b) It also differs from the method which claims to use a polyol as the sole stabilizer. Pasteurization using only a polyol in the absence of any glycine results in relatively poor recovery of, for example, Factor VIII activity. It is also apparent that the final formulations of the reference products contain glycine and, therefore, the pasteurization conditions resemble those using a sugar in combination with an amino acid.

The object of the present invention is to provide a method for inactivating viruses and bacteria in biological and pharmaceutical products while maintaining and recovering maximal biological or pharmaceutical activity. The object is achieved by the utilization of thermal or chemical inactivation processes that are known to deactivate viruses and bacteria while using stabilizing agents to prevent or inhibit loss of activity of the products.

SUMMARY OF THE INVENTION

According to the invention, a method of inactivating pathogens in biological and pharmaceutical products is provided, which comprises:

mixing the product in aqueous solution with one or more primary stabilizers selected from the group consisting of mono-, di-, or tri-saccharides or sugar alcohols having a concentration of 10% w/v to saturation;

adding one or more secondary stabilizers selected from the group consisting of neutral salts at concentrations of 0.01M to saturation to obtain a mixture;

thermally inactivating pathogens by maintaining a temperature of 30° C. to 100° C. for 1 minute to 72 hours;

adjusting the pH to a range of 5.0 to 10.0 and preferably to 6.7 to 7.7; and removing said primary and secondary stabilizers after thermal inactivation.

DETAILED DESCRIPTION OF THE INVENTION

Description of the Preferred Embodiment

In accordance with the present invention, biological and pharmaceutical products are pasteurized in the presence of primary and secondary stabilizers, the combined effect of which insures that the products' activity is preserved during the heating process.

The heat treatment is carried out at a temperature and for a period of time sufficient to inactivate the pathogens, especially infectious viruses, but at the same time to retain the activity of the products. Such heat treatment is maintained for about 1 minute to 72 hours at a temperature of 30° C. to 100° C., preferably for about 10 to 20 hours at 55° C. to 70° C., and most preferably for 10 hours at 60° C.

In freeing the biological/pharmaceutical products from pathogens, an aqueous medium is employed in which are dissolved or suspended the primary and secondary stabilizers. The product to be pasteurized is contacted with the medium and subjected to pasteurizing conditions sufficient to deactivate pathogens. Treatment of the product can be carried out at any stage in the production process, such as the starting material stage or at some later step in the production sequence, or with certain products, after completion of the production process.

Following the addition of the stabilizers, the pH is adjusted, if necessary, to a range of 5.0 to 10.0 and preferably to 6.7 to 7.7. Product concentration in the aqueous medium will generally range from about 1 mg/ml to about 500 mg/ml and more preferably from about 1 to 100 mg/ml.

After pasteurization is complete, the stabilizers are removed by appropriate means which include: dialysis (McPhie, P. (1971), Methods in Enzymol. 22, pp. 23-32); diafiltration (Blatt, W. F. et al. (1968) Anal. Biochem. 26, p. 151); column chromatography (Porath, J. and Flodin, P. (1959), Nature 183, pp. 1657-1659); precipitation (Dixon, M. and Webb, E. C. (1961), Adv. in Protein Chem. 16, pp. 197-219, Academic Press, N.Y.; Honig, W. and Kula, M. R. (1976) Anal. Biochem. 72, pp. 502-512); or any other method by which removal of the stabilizers can be effected.

Products

The process of the present invention is applicable to a great number and variety of materials and products in the biomedical and pharmaceutical fields intended to be used in the human or animal body for biomedical or therapeutic purposes as well as non-therapeutic experimental purposes. Contemplated materials and products which can be made free of pathogens using the process of the present invention include but are not limited to: blood fractions such as antihemophilic factor (Smith, J. K. and Bidwell, E. (1979) Clinics in Hoematol. 8, pp. 184-205); prothrombin complex, i.e., Factors II, VII, IX, and X (Chandra, S. and Brummelhuis, H. G. J. (1981) Vox Sang. 41, pp. 257-273); Protein C (Stenflo, J. (1976) J. Biol. Chem. 251, pp. 355-363 and Bajaj, S. P. et al. (1983) Prep. Biochem. 13, pp. 191-214); Protein S (DiScipio, R. G., et al. (1977) Biochemistry 16, pp. 698-706); Antithrombin III (Rosenberg, R. D., and Damus, P. S. (1973) J. Biol Chem. 248, pp. 6490-6505); C-1 esterase inhibitor (Heimburger, N. (1974) Bayer Symposium V "Proteinase Inhibitors", pp. 14-22, Springer-Verlag); alpha 1 antitrypsin (Heimburger, N. supra.); Fibronectin (Mosesson, M. N. and Amrani, D. L. (1980), Blood 56 pp. 145-158); Gamma Globulin (Oncley et al. (1949) J. Amer. Chem. Soc. 71, pp. 541-550); biological or pharmaceutical products derived from human or animal origin such as insulin, enzymes, coenzymes, antibodies and hormones; biological or pharmaceutical products derived from human or animal placentae such as blood fractions and vaccines; biological or pharmaceutical products derived by recombinant DNA techniques and produced in bacteria, fungi, or mammalian cell culture systems (Vane, J. and Cuatrecases, P. (1984), Nature 312, pp. 303-305 and Maniatis, T. et al. (1982), Molecular Cloning: A Laboratory Manual, Cold Spring Harbor, N.Y.). These products and materials are available from various commercial sources or can be produced by using well-known preparative techniques. For example, blood fractions and blood proteins can be obtained from human blood plasma by fractionation according to known techniques such as, for example, the alcohol fractionation of Cohn described in U.S. Pat. No. 2,390,074 and the Journal of the American Chemical Society Vol. 68, p. 459 (1946). These methods as well as other techniques are summarized in "The Plasma Proteins", second edition, Vol. III, pp. 548-550, Academic Press, New York, N.Y. (1977).

Primary Stabilizers

The primary stabilizers include mono-, di-, or tri-saccharides, and sugar alcohols, e.g., glucose, sucrose, xylose, fructose and mannitol, glucosaminitol, sorbitol, galactosaminitol and the like. One or more of these stabilizers are used in the process of the present invention at a concentration range of 10% w/v to saturation.

The preferred primary stabilizer is sucrose at a concentration of about 50% to 70% w/v.

Secondary Stabilizers

The secondary stabilizers consist of certain neutral salts and are used in the process of the present invention at a concentration of 0.01M to saturation. The preferred stabilizing salts are defined for the purposes of this invention as neutral salts of common organic and mineral acids as exemplified by, but not limited to, sodium acetate, potassium acetate, sodium phosphate, sodium sulfate, and ammonium sulfate, as well as lithium sulfate, potassium sulfate, magnesium sulfate, barium sulfate, lithium acetate, magnesium acetate, and barium acetate and as referenced by the following:

1. Molecular Biology of Human Proteins, Vol. 1, page 3, 1966. Schultze, H. E. and Heremans, J. F.
2. Biophysical Chemistry, Vol. 1, pages 275-277, 1958. Edsall, J. T. and Wyman, J.
3. Handbook of Chemistry and Physics, CRC Handbook, 57th Edition, page 113, 1976-1977.
4. Textbook of Biochemistry, 3rd. Edition, page 96, 1963. West, E. S. and Todd, W. R.

The concentration of the stabilizing salt to be used is dependent upon two parameters. First, it depends upon the solubility of the molecule, and second, the concentration at which salting out of the protein(s) begins to occur in the solution.

The following examples will further illustrate the invention although it will be understood that the invention is not limited thereto.

EXAMPLE 1

Pasteurization of a Low-Fibrinogen AHF Concentrate Stabilization by Sucrose+Sodium Acetate Each of three vials of Factorate-LF ®(low-fibrinogen Factor VIII produced by Armour Pharmaceutical Company, Kankakee, Ill.) was reconstituted in 10 ml of water for injection. To one was added 1.0 g sucrose per ml of solution plus 0.5 g sodium acetate per ml of solution. To another was added 1.0 g sucrose per ml of solution. No stabilizers were added to the third vial. The pH of the three solutions was adjusted to 7.0 using a small amount of 0.5N hydrochloric acid. The solutions were heated at 60° C. for 10 hours. Samples before and after pasteurization from each solution were assayed for procoagulant activity (F.VIII:C) by the one stage Activated Partial Thromboplastin Time (APTT) method which is essentially the same as the methods described by Hardisty, R. M. and MacPherson, J. C. (1962), Thrombosis et Diathesis Haemorrhagica 7, pp. 215-229 and Zacharski, L. R. and Rosenstein, R. (1978), Amer. J. Clin. Path. 70, pp. 280-286. The results are summarized in Table 1.

TABLE 1

| Stabilizers | F.VIII Units/ml Before Pasteurization | F.VIII Units/ml After Pasteurization | % Recovery |
|---|---|---|---|
| Sucrose + Sodium Acetate: | 11.4 | 9.2 | 80.7 |
| Sucrose: | 14.2 | 5.9 | 41.5 |
| None: | 20.1 | 0 | 0 |

EXAMPLE 2

Pasteurization of Highly Purified Factor VIII:C Stabilization by Sucrose + Sodium Acetate Monoclate ® Factor VIII:C, produced by Armour Pharmaceutical Company, Kankakee, Ill.) was pasteurized in the following manner. Three aliquots of 10 ml each (approximately 500 units) of ultrafiltered eluate from an anti-F.-VIII:R-Sepharose-Cl-2B column were used. The first was mixed with 1.0 g sucrose per ml of solution plus 0.5 g sodium acetate per ml of solution. To the second aliquot was added 1.0 g sucrose per ml of solution. No stabilizers were added to the third aliquot. The pH of the three solutions was adjusted to 7.0 with a small amount of 0.5N hydrochloric acid. The solutions were heated at 60° C. for 10 hours. Samples before and after pasteurization were assayed for procoagulant activity (F.VIII:C) by the one stage APTT method referred to in Example 1. The results are summarized in Table 2.

TABLE 2

| Stabilizers | F.VIII Units/ml | | % Recovery |
| --- | --- | --- | --- |
| | Before Pasteurization | After Pasteurization | |
| Sucrose + Sodium Acetate: | 17.6 | 10.4 | 60.2 |
| Sucrose: | 23.2 | 6.7 | 28.9 |
| None: | 23.0 | 1.0 | 4.0 |

EXAMPLE 3

Pasteurization of Highly Purified Factor VIII:C Stabilization by Sucrose + Sodium Sulfate Monoclate ® (Factor VIII:C, produced by Armour Pharmaceutical Company, Kankakee, IL) was pasteurized in the following manner. Two aliquots of 10 ml each (approximately 500 units) of ultrafiltered eluate from an anti-F.VIII:R-Sepharose-Cl-2B column were used. The first was mixed with 1.0 g sucrose per ml of solution plus 0.28 g sodium sulfate per ml of solution. To the second aliquot was added 1.0 g sucrose per ml of solution. The pH of the two solutions was adjusted to 7.0 with a small amount of 0.5N hydrochloric acid. The solutions were heated at 60° C. for 10 hours. Samples before and after pasteurization were assayed for procoagulant activity (F.VIII:C) by the one stage APTT method referred to in Example 1. The results are summarized in Table 3.

TABLE 3

| Stabilizers | F.VIII Units/ml | | % Recovery |
| --- | --- | --- | --- |
| | Before Pasteurization | After Pasteurization | |
| Sucrose + Sodium Sulfate: | 21.5 | 17.6 | 81.9 |
| Sucrose: | 20.0 | 5.7 | 28.5 |

EXAMPLE 4

Pasteurization of a Low-Fibrinogen AHF Concentrate Stabilization by Sucrose + Various Neutral Salts Each of nine vials of Factorate-LF ® (low-fibrinogen Factor VIII produced by Armour Pharmaceutical Company, Kankakee, Ill.) was reconstituted in 10 ml of water for injection. After reconstitution was completed, 1.0 g sucrose per ml of solution was added to each. Different stabilizing salts were then added, at concentrations of 1-2M, to each of the Factorate-LF ® (sucrose solutions. The salts used were: potassium acetate (2.0 g), ammonium acetate (1.6 g), sodium sulfate (2.8 g), ammonium sulfate (2.6 g), sodium chloride (1.2 g), ammonium chloride (1.1 g), magnesium chloride (0.95 g), choline chloride (2.8 g), and sodium phosphate, dibasic (1.4 g). The pH of the solutions was then adjusted to 7.0 using either 0.5N hydrochloric acid or 0.5N sodium hydroxide, except for the solution containing sodium phosphate. The pH of this solution was 8.2, unadjusted. The solutions were heated at 60° C. for 10 hours. Samples before and after pasteurization from each solution were assayed for procoagulant activity (F.VIII:C) by the one stage APTT method referred to in Example 1. The results are summarized in Table 4.

TABLE 4

| Stabilizers | % Recovery of F.VIII After Pasteurization |
| --- | --- |
| Sucrose + Potassium Acetate | 89.4 |
| Sucrose + Ammonium Acetate | 72.7 |
| Sucrose + Sodium Sulfate | 89.1 |
| Sucrose + Ammonium Sulfate | 78.6 |
| Sucrose + Sodium Chloride | 16.7 |
| Sucrose + Ammonium Chloride | 34.7 |
| Sucrose + Magnesium Chloride | 10.9 |
| Sucrose + Choline Chloride | 10.0 |
| Sucrose + Sodium Phosphate (Dibasic) | 28.0 |

EXAMPLE 5

Pasteurization of a High-Fibrinogen AHF in Al(OH)3 Adsorbed Cryoprecipitate/Stabilization by Sucrose + Potassium Acetate Human cryoprecipitate was suspended in four (4) volumes of buffer containing 0.05 m glycine and 0.04 m sodium chloride, pH 6.90±0.10. The dissolved cryoprecipitate was treated twice with approximately 20 ml of 2% Al(OH)3 per kilogram of solution followed by centrifugation, to remove vitamin K dependent factors (proteases). After the second centrifugation, pasteurization stabilizers were added to the Factor VIII solution using 70% w/v sucrose and 7% w/v potassium acetate, followed by heataing at 60° C. for 10 hours.

EXAMPLE 6

Pasteurization of a High-Fibrinogen AHF Stabilization by Sucrose + Potassium Acetate One (1) vial of Factorate ® (Trademark for Factor VIII produced by Armour Pharmaceutical Company, Kankakee, Ill.), having specific activity of approximately 0.5 Factor VIII units per mg of protein, was reconstituted in 20 ml water for injection. Pasteurization stabilizers were added using -]70% w/v sucrose and 7% w/v potassium acetate, followed by heating at 60° C. for 10 hours.

EXAMPLE 7

Pasteurization of a High-Fibrinogen AHF Stabilization by Sucrose + Potassium Acetate One (1) vial of Factorate ® Generation II (Trademark for Factor VIII produced by Armour Pharmaceutical Company, Kankakee, Ill.), having specific activity of approximately 3.0 Factor VIII units per mg of protein, was reconstituted in 20 ml water for injection. Pasteurization stabilizers were added using 70% w/v sucrose and 7% w/v potassium acetate, followed by heating at 60° C. for 10 hours.

Samples of Examples 5–7 before and after pasteurization were assayed for procoagulant activity by the one stage APTT method referred to in Example 1. The results are shown in Table 5.

TABLE 5

| | F.VIII Units/ml | | % Recovery |
| --- | --- | --- | --- |
| | Before Pasteurization | After Pasteurization | |
| Example 5 | 2.56 | 2.46 | 96 |
| Example 6 | 8.4 | 7.0 | 83 |
| Example 7 | 32.4 | 31.0 | 96 |

The following conclusions are readily apparent from the tests described by the examples and the results shown in the Tables pasteurization of the proteinaceous materials at 60° C. for 10 hours results in close to complete destruction of their activity; while the use of a sugar alone (sucrose) improves the retention of activity, it is considerably less effective than when a combination of a sugar and certain of the stabilizing salts are employed as stabilizers and; the combination of a sugar with certain stabilizing salts as stabilizers is superior to the combination of a sugar and other stabilizing salts.

Viral Inactivation (a) Representative viral inactivation data obtained on biological products treated according to the present invention is illustrated by the following.

EXAMPLES 8, 9 and 10

HIV Infectivity Following Pasteurization

Example 8

An aqueous solution containing low fibrinogen Factor VIII, 70% w/v sucrose and 7% w/v potassium acetate was inoculated with AIDS virus (LAV stain of HIV-1) followed by heating at 60° C. for 10 hours.

Example 9

An aqueous solution containing Factor VIII (ultrafiltered eluate from an anti-F.VIII:R-Sepharose- Cl-2B column), 70% w/v sucrose and 7% w/v potassium acetate was inoculated with AIDS viruse (LAV strain of HIV-1) followed by heating at 60° C. for 10 hours.

Example 10

Resuspended cryoprecipitate (Al(OH)3 adsorbed) containing 60% w/v sucrose and 1 M NaCl was inoculated with AIDS virus (LAV strain of HIV-1) followed by heating at 60° C. for 10 hours.

(b) After completion of heating, each solution (using unheated solutions as controls) was tested for HIV infectivity by serial dilution, followed by inoculation of CEM cells. Inoculations were performed in duplicate for each dilution, the flasks were gassed with 5% $CO_2$/95% air and incubated at 37° C. The cells were observed weekly for cytopathic effects for six weeks and the titers and reductions were calculated from these observations. The results, demonstrating highly effective reductions in viral infectivity, are shown in Table 6.

TABLE 6

HIV Infectivity Following Pasteurization
Infectivity Expressed in $Log_{10}$

|  | Initial | After Pasteurization | Reduction |
|---|---|---|---|
| Example 8 | 11.0 | 0.5 | 10.5 |
| Example 9 | 10.8 | 0.5 | 10.3 |
| Example 10 | 11.0 | 0.2 | 10.8 |

(c) To maintain bilogical stability on storage of various products, it is necessary and/or desirable to preserve them in a freeze-dried form. While freeze-drying is not part of the present invention, it is an essential step in the preservation of various pharmaceutical and biological products to which the invention relates. Example illustrates the preparatory sequence for such a product.

EXAMPLE 11

Preparation of a Highly Purified F.VIII

Cryoprecipitate was suspended in 5% ethyl alcohol, the pH and temperature were adjusted to remove fibrinogen, Al(OH)3 was added, and the solution was clarified by centrifugation and filtration. The filtrate was diafiltered to remove alcohol and then pasteurization stabilizers were added, using 70% w/v sucrose and 7% w/v potassium acetate. The solution was heated at 60° C. for 10 hours. After pasteurization, the solution was applied to an anti-F.VIII:R-Sepharose CL-2B (MAb) column. The eluate was concentrated by ultrafiltration and applied to an AH-Sepharose column. The eluate was dialyzed and sterile filtered resulting in a highly purified F.VIII which was then filled into vials and freeze-dried.

Other Embodiments

In accordance with another embodiment of the present invention, stabilization of biological or pharmaceutical products can also be obtained when methods other than pasteurization are used for bacterial and viral inactivation. These methods include: chemical inactivation, such as, using ozone as the pathogen deactivating agent, as described in U.S. Pat. No. 4,632,980, using an organic compound to promote deactivation as described in U.S. Pat. No. 4,640,834; or using high energy (UV, infrared, and gamma) irradiation as described by U.S. Pat. No. 2,897,123.

It is apparent that numerous modifications and variations of the invention may be made without departing from the spirit and scope thereof. The specific embodiments described are given by way of example only, and the invention is limited only by the scope of the appended claims.

What is claimed is:

1. A method of inactivating pathogens in a proteinaceous biological or a proteinaceous pharmaceutical product comprising the steps of:
    mixing said product in an aqueous solution containing at least one primary stabilizer selected from the group consisting of sugars and sugar alcohols and at least one secondary stabilizer selected from the group consisting of neutral salts;
    adjusting the pH of said aqueous solution to about 5.0 to 10.0;
    subjecting said aqueous solution to a pathogen inactivating process; and
    optionally removing said primary and secondary stabilizers from said aqueous solution.

2. The method of claim 1 wherein said pathogen inactivating process comprises subjecting said aqueous solution to a temperature of 30° C. to 100° C. for about 1 minute to 72 hours.

3. The method of claim 1 wherein said pathogen inactivating process comprises chemical inactivation.

4. The method of claim 3 wherein said chemical inactivation is by ozone.

5. The method of claim 3 wherein said chemical inactivation is by ethylene oxide.

6. The method of claim 1 wherein said pathogen inactivation is by irradiation.

7. The method of claim 6 wherein said irradiation is by ultraviolet rays.

8. The method of claim 6 wherein said irradiation is by infrared rays.

9. The method of claim 6 wherein said irradiation by gamma rays.

10. A proteinaceous product having been treated at any desired stage of its production to inactivate pathogens therein by a method which comprises the steps of:
mixing said product in an aqueous solution containing at least one primary stabilizer selected from the group consisting of sugars and sugar alcohols and at least one secondary stabilizer selected from the group consisting of sodium acetate, potassium acetate, sodium sulfate, ammonium sulfate, lithium sulfate, potassium sulfate, magnesium sulfate, lithium acetate, magnesium acetate, ammonium acetate and barium acetate;
adjusting the pH of said aqueous solution to about 5.0 to 10.0;
subjecting said aqueous solution to a pathogen inactivating process.

11. A method of inactivating pathogens in a proteinaceous biological or a proteinaceous pharmaceutical material comprising the steps of:
contacting said material with an aqueous solution of at least one primary stabilizer selected from the group consisting of mono-, di-, tri-saccharides and sugar alcohols and at least one secondary stabilizer selected from the group consisting of sodium acetate, potassium acetate, sodium sulfate, ammonium sulfate, lithium sulfate, potassium sulfate, magnesium sulfate, barium sulfate, lithium acetate, magnesium acetate, and barium acetate;
adjusting the pH of said aqueous solution to about 6.7 to 7.7;
subjecting said aqueous solution to pasteurization conditions sufficient to deactivate pathogens therein; and
optionally removing said primary and secondary stabilizers from said aqueous solution.

12. The method of claim 11 wherein said sugars are glucose, sucrose, xylose, fructose, mannitol, and said sugar alcohols are galactitol, glucosaminitol, sorbitol and galactosaminitol.

13. The method of claim 11 wherein said pasteurization is carried out at a temperature of about 55° C. to 70° C. for 10 to 20 hours.

14. The method of claim 11 wherein removal of primary and secondary stabilizers is by dialysis.

15. The method of claim 11 wherein removal of primary and secondary stabilizers is by diafiltration.

16. The method of claim 11 wherein removal of primary and secondary stabilizers is by column chromatography.

17. The method of claim 11 wherein removal of primary and secondary stabilizers is by precipitation.

18. The method of claim 11 wherein said material is a plasma protein derived from human or animal sources.

19. The method of claim 18 wherein said plasma protein is derived from human or animal placentae.

20. The method of claim 11 wherein said material is an enzyme, coenzyme, hormone or insulin.

21. The method of claim 11 wherein said material is the starting material constituting the active component in a finished product.

22. The method of claim 11 wherein said material is in a processing stage of the finished product.

23. The method of claim 11 wherein said material is the finished product.

24. The method of claim 11 wherein said material is dissolved in said aqueous solution.

25. The method of claim 11 wherein said material is suspended in said aqueous solution.

26. A proteinaceous product having been treated at any desired stage of its production to inactivate pathogens therein by a method which comprises the steps of:
contacting said product with an aqueous solution of at least one primary stabilizer selected from the group consisting of mono-, di-, tri-saccharides and sugar alcohols and at least one secondary stabilizer selected from the group consisting of sodium acetate, potassium acetate, sodium sulfate, ammonium sulfate, lithium sulfate, potassium sulfate, magnesium sulfate, barium sulfate, lithium acetate, magnesium acetate, and barium acetate;
adjusting the pH of said aqueous solution to about 6.7 to 7.7;
subjecting said aqueous solution to pasteurization conditions sufficient to deactivate pathogens therein.

27. A method of inactivating pathogens in a proteinaceous biological or a proteinaceous pharmaceutical material comprising the steps of:
heating said material in an aqueous solution for about 10 hours at about 60° C. in the presence of
(a) 10% w/v to saturation of at least one primary stabilizer selected from the group consisting of glucose, sucrose, xylose, fructose, mannitol, galactitol, glucosaminitol, sorbitol, and galactosaminitol; and
(b) 0.01M to saturation of at least one secondary stabilizer selected from the group consisting of sodium acetate, potassium acetate, sodium sulfate, ammonium sulfate, lithium sulfate, potassium sulfate, magnesium sulfate, barium sulfate, lithium acetate, magnesium acetate, and barium acetate;
(c) optionally separating said primary and secondary stabilizers from said aqueous solution.

28. The method of claim 27 wherein said primary stabilizer is sucrose at a concentration of about 50% w/v to 70% w/v.

29. The method of claim 27 wherein said secondary stabilizer is sodium acetate at a concentration of about 0.5M to about 2.5M.

30. The method of claim 27 wherein said material is Factor VIII.

31. The method of claim 27 wherein said material is prothrombin complex.

32. A proteinaceous product having been treated at any desired stage of its production to inactivate pathogens therein by a method which comprises the steps of:
heating said product in an aqueous solution for about 10 hours at about 60° C. in the presence of
(a) 10% w/v to saturation of at least one primary stabilizer selected from the group consisting of glucose, sucrose, xylose, fructose, mannitol, galactitol, glucosaminitol, sorbitol, and galactosaminitol; and
(b) 0.01M to saturation of at least one secondary stabilizer selected from the group consisting of sodium acetate, potassium acetate, sodium sulfate, ammonium sulfate, lithium sulfate, potassium sulfate, magnesium sulfate, barium sulfate, lithium acetate, magnesium acetate, and barium acetate.

* * * * *

UNITED STATES PATENT AND TRADEMARK OFFICE
CERTIFICATE OF CORRECTION

PATENT NO. : 4,876,241
DATED : October 24, 1989
INVENTOR(S) : Feldman, et al.

It is certified that error appears in the above-identified patent and that said Letters Patent is hereby corrected as shown below:

In column 10, line 46 delete [neutral salts;] and insert sodium acetate, potassium acetate, sodium sulfate, ammonium sulfate, lithium sulfate, potassium sulfate, magnesium sulfate, lithium acetate, magnesium acetate, ammonium acetate and barium acetate; therefor.

In column 11, line 1 after the word "irradiation" insert --is--.

Signed and Sealed this

Twenty-second Day of June, 1993

Attest:

MICHAEL K. KIRK

Attesting Officer

Acting Commissioner of Patents and Trademarks